United States Patent
Liu et al.

(10) Patent No.: US 10,660,560 B2
(45) Date of Patent: May 26, 2020

(54) PREDICTIVE FALL PREVENTION USING CORRECTIVE SENSORY STIMULATION

(71) Applicant: International Business Machines Corporation, Armonk, NY (US)

(72) Inventors: Su Liu, Austin, TX (US); Inseok Hwang, Austin, TX (US); Eric J. Rozner, Austin, TX (US); Jinho Lee, Austin, TX (US)

(73) Assignee: International Business Machiness Corporation, Armonk, NY (US)

( * ) Notice: Subject to any disclaimer, the term of this patent is extended or adjusted under 35 U.S.C. 154(b) by 0 days.

(21) Appl. No.: 16/114,100

(22) Filed: Aug. 27, 2018

(65) Prior Publication Data
US 2020/0060601 A1 Feb. 27, 2020

(51) Int. Cl.
*H04W 88/02* (2009.01)
*A61B 5/00* (2006.01)
*G06F 3/01* (2006.01)
*A61N 1/36* (2006.01)

(52) U.S. Cl.
CPC ........ *A61B 5/4023* (2013.01); *A61N 1/36003* (2013.01); *A61N 1/36036* (2017.08); *G06F 3/011* (2013.01)

(58) Field of Classification Search
CPC ............ A61N 1/36036; A61N 1/36003; A61B 5/4836; G06F 3/011; A61H 3/00; A61H 1/0266; A61H 1/0244; G06K 9/00805; G01B 11/026
See application file for complete search history.

(56) References Cited

U.S. PATENT DOCUMENTS

| | | | |
|---|---|---|---|
| 5,762,612 A | 6/1998 | Campbell | |
| 6,077,237 A | 6/2000 | Campbell et al. | |
| 6,219,578 B1 | 4/2001 | Collins et al. | |
| 6,546,291 B2 | 4/2003 | Merfeld et al. | |
| 8,718,796 B2 | 5/2014 | Cevette et al. | |
| 2005/0146600 A1* | 7/2005 | Chipchase | H04M 1/72522 348/14.02 |

(Continued)

OTHER PUBLICATIONS

Fitzpatrick et al., "Resolving Head Rotation for Human Bipedalism," Current Biology, vol. 16, Aug. 8, 2006, pp. 1509-1514.

(Continued)

*Primary Examiner* — An T Nguyen
(74) *Attorney, Agent, or Firm* — Zilka-Kotab, P.C.

(57) ABSTRACT

A computer-implemented method according to one embodiment includes performing a survey of a survey area of a surface in an intended direction of travel of a user, determining whether an obstacle is present in the survey area of the surface within a predetermined distance of the user, and in response to determining that a detected obstacle is present in the survey area of the surface within the predetermined distance of the user, performing a process until it is determined that the obstacle is not present in the survey area of the surface within the predetermined distance of the user. The process includes determining a corrective sensory stimulation for offsetting balance of the user in a direction away from the obstacle, and outputting the corrective sensory stimulation to a sensory user device.

16 Claims, 8 Drawing Sheets

(56) References Cited

U.S. PATENT DOCUMENTS

| | | | |
|---|---|---|---|
| 2007/0255322 A1* | 11/2007 | Gerber | A61N 1/37247 607/2 |
| 2010/0114256 A1 | 5/2010 | Chan et al. | |
| 2011/0044604 A1* | 2/2011 | Brokken | G06F 3/016 386/239 |
| 2011/0143816 A1* | 6/2011 | Fischer | G08G 1/16 455/566 |
| 2012/0101411 A1* | 4/2012 | Hausdorff | A61B 5/1117 600/595 |
| 2013/0218456 A1 | 8/2013 | Zelek et al. | |
| 2014/0080540 A1* | 3/2014 | Hsiao | H04M 1/0264 455/556.1 |
| 2014/0142839 A1* | 5/2014 | Kaminade | G08G 1/166 701/301 |
| 2015/0032186 A1 | 1/2015 | Cushing et al. | |
| 2016/0247030 A1* | 8/2016 | Matsumoto | B60R 1/00 |
| 2017/0165481 A1 | 6/2017 | Menon | |
| 2017/0286783 A1* | 10/2017 | Yim | G01B 11/00 |
| 2017/0303849 A1* | 10/2017 | De Sapio | A61B 5/1117 |
| 2018/0005421 A1* | 1/2018 | Park | G06T 11/60 |
| 2018/0344561 A1* | 12/2018 | Komatsu | A61H 3/00 |

OTHER PUBLICATIONS

Tang et al., "iPrevent: A Novel Wearable Radio Frequency Range Detector for Fall Prevention," IEEE, 2016, 3 pages.

Sra, M., "Asymmetric Design Approach and Collision Avoidance Techniques for Room-scale Multiplayer Virtual Reality," UIST'16 Adjunct, Oct. 2016, pp. 29-32.

Cai et al., "Galvanic Vestibular Stimulation (GVS) Augments Deficient Pedunculopontine Nucleus (PPN) Connectivity in Mild Parkinson's Disease: fMRI Effects of Different Stimuli," Frontiers in Neuroscience, Feb. 28, 2018, pp. 1-13.

NCOA, "Falls Prevention Facts," national Council on Aging, 2018, 4 pages, retrieved from https://www.ncoa.org/news/resources-for-reporters/get-the-facts/falls-prevention-facts/.

Wired, "Hacking the Inner Ear for VR—And for Science," Wired, 2018, 10 pages, retrieved from https://www.wired.com/2015/09/hacking-inner-ear-vrand-science/.

Lan et al., "SmartFall: An Automatic Fall Detection System Based on Subsequence Matching for the SmartCane," BodyNets, Apr. 2009, 8 pages.

Fang et al., "Developing a Mobile Phone-based Fall Detection System on Android Platform," IIEEE ComComAp'12, 2012, pp. 143-146.

Byrne et al., "Balance Ninja: Towards the Design of Digital Vertigo Games via Galvanic Vestibular Stimulation," CHI Play '16 CD-ROM, Oct. 2016, 13 pages.

Engadget, "These smart shoes alert you if your grandma falls," CES, 2018, 11 pages, retrieved from https://www.engadget.com/2018/01/07/e-vone-smart-shoes/.

Life Alert, "Help! I've Fallen and I can't get up!" 2018, 3 pages, retrieved from http://www.lifealert.com/.

Wired, "This smart exoskeleton predicts when the elderly are going to fall and keeps them on their feet," May 2017, 6 pages, retrieved from http://www.wired.co.uk/article/exoskeleton-stop-falls-elderly.

Techcrunch, "The B-Shoe hopes to prevent seniors from falling down," 2018, 7 pages, retrieved from https://techcrunch.com/2017/07/02/the-b-shoe-hopes-to-prevent-seniors-from-falling-down/.

Shelton et al., "Comparison between Auditory and Visual Simple Reaction Times," Neuroscience & Medicine, 2010, vol. 1, pp. 30-32.

Lam et al., "The medium latency muscle response to a vestibular perturbation is increased after depression of the cerebellar vermis," Journal of Brain and Behavior, Jun. 2017, pp. 1-9.

Montanini et al., "A Footwear-Based Methodology for Fall Detection," IEEE Sensors Journal, vol. 18, No. 3, Feb. 1, 2018, pp. 1233-1242.

* cited by examiner

US 10,660,560 B2

PREDICTIVE FALL PREVENTION USING CORRECTIVE SENSORY STIMULATION

BACKGROUND

The present invention relates to user assistance devices, and more specifically, this invention relates to use of corrective sensory stimulation for preventing humans from suffering from obstacle-related fall events.

Walking surfaces are often uneven or stricken with one or more obstacles, which causes difficulty for walking thereon. Many times, obstacles go unnoticed by someone traversing walking surfaces with obstacles, and as a result the obstacles influence such people to trip, fall, roll an ankle, etc.

Older adults are especially prone to falling, e.g., as a result of poor eyesight, as a result of diminished balance, as a result of diminished reflex timing, etc., after contacting such obstacles. These adults are often injured as a result of such falls. However, such obstacle related injuries are a threat to persons of all age groups.

SUMMARY

A computer-implemented method according to one embodiment includes performing a survey of a survey area of a surface in an intended direction of travel of a user, determining whether an obstacle is present in the survey area of the surface within a predetermined distance of the user, and in response to determining that a detected obstacle is present in the survey area of the surface within the predetermined distance of the user, performing a process until it is determined that the obstacle is not present in the survey area of the surface within the predetermined distance of the user. The process includes determining a corrective sensory stimulation for offsetting balance of the user in a direction away from the obstacle, and outputting the corrective sensory stimulation to a sensory user device.

A computer program product for preventing user falls according to one embodiment includes a computer readable storage medium having program instructions embodied therewith. The computer readable storage medium is not a transitory signal per se. The program instructions are readable and/or executable by a computer to cause the computer to perform, by the computer, the foregoing method.

An apparatus according to one embodiment includes a camera for capturing image data of a survey area of a surface in a direction of travel of a user, a processor coupled to the camera for analyzing the image data for determining whether an obstacle is present in the survey area of the surface within a predetermined distance of the user, and for, in response to determining an obstacle is present in the survey area of the surface within the predetermined distance of the user, outputting an instruction to apply a corrective sensory stimulation for offsetting balance of the user in a direction away from the obstacle. The apparatus further includes a sensory user device coupled to the processor for applying the corrective sensory stimulation to the user in response to receiving the instruction.

Other aspects and embodiments of the present invention will become apparent from the following detailed description, which, when taken in conjunction with the drawings, illustrate by way of example the principles of the invention.

DETAILED DESCRIPTION

Figure 1:
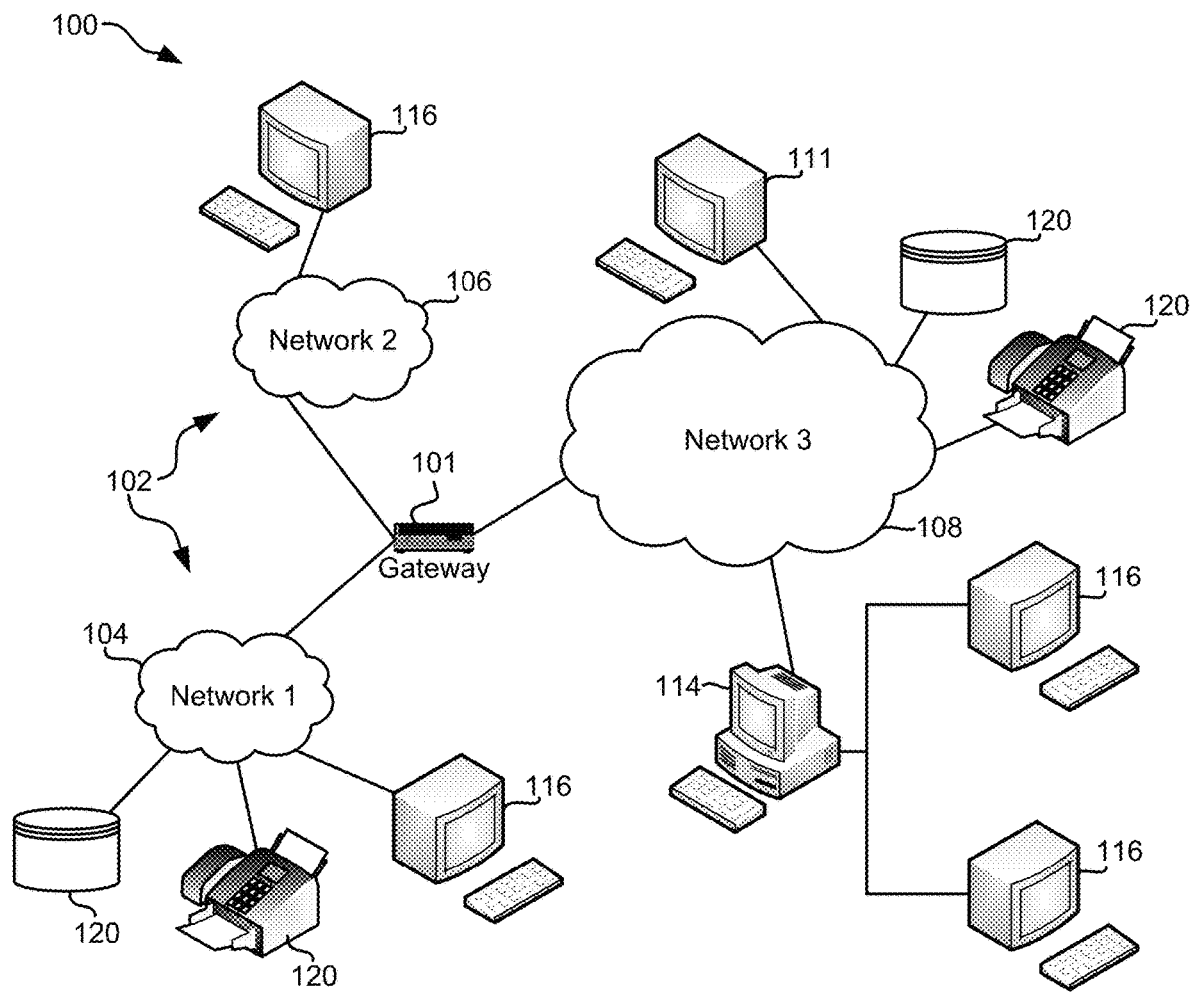
FIG. 1 is a network architecture, in accordance with one embodiment.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The following description discloses several preferred embodiments of systems, methods and computer program products for predictive fall prevention using corrective sensory stimulation induced intervention.

In one general embodiment, a computer-implemented method includes performing a survey of a survey area of a surface in an intended direction of travel of a user, determining whether an obstacle is present in the survey area of the surface within a predetermined distance of the user, and in response to determining that a detected obstacle is present in the survey area of the surface within the predetermined distance of the user, performing a process until it is determined that the obstacle is not present in the survey area of the surface within the predetermined distance of the user. The process includes determining a corrective sensory stimulation for offsetting balance of the user in a direction away from the obstacle, and outputting the corrective sensory stimulation to a sensory user device.

In another general embodiment, a computer program product for preventing user falls includes a computer readable storage medium having program instructions embodied therewith. The computer readable storage medium is not a transitory signal per se. The program instructions are readable and/or executable by a computer to cause the computer to perform, by the computer, the foregoing method.

In another general embodiment, an apparatus includes a camera for capturing image data of a survey area of a surface in a direction of travel of a user, a processor coupled to the camera for analyzing the image data for determining whether an obstacle is present in the survey area of the surface within a predetermined distance of the user, and for, in response to determining an obstacle is present in the survey area of the surface within the predetermined distance of the user, outputting an instruction to apply a corrective sensory stimulation for offsetting balance of the user in a direction away from the obstacle. The apparatus further includes a sensory user device coupled to the processor for applying the corrective sensory stimulation to the user in response to receiving the instruction.

FIG. 1 illustrates an architecture 100, in accordance with one embodiment. As shown in FIG. 1, a plurality of remote networks 102 are provided including a first remote network 104 and a second remote network 106. A gateway 101 may be coupled between the remote networks 102 and a proximate network 108. In the context of the present architecture 100, the networks 104, 106 may each take any form including, but not limited to a local area network (LAN), a wide area network (WAN) such as the Internet, public switched telephone network (PSTN), internal telephone network, etc.

In use, the gateway 101 serves as an entrance point from the remote networks 102 to the proximate network 108. As such, the gateway 101 may function as a router, which is capable of directing a given packet of data that arrives at the gateway 101, and a switch, which furnishes the actual path in and out of the gateway 101 for a given packet.

Further included is at least one data server 114 coupled to the proximate network 108, and which is accessible from the remote networks 102 via the gateway 101. It should be noted that the data server(s) 114 may include any type of computing device/groupware. Coupled to each data server 114 is a plurality of user devices 116. User devices 116 may also be connected directly through one of the networks 104, 106, 108. Such user devices 116 may include a desktop computer, lap-top computer, hand-held computer, printer or any other type of logic. It should be noted that a user device 111 may also be directly coupled to any of the networks, in one embodiment.

A peripheral 120 or series of peripherals 120, e.g., facsimile machines, printers, networked and/or local storage units or systems, etc., may be coupled to one or more of the networks 104, 106, 108. It should be noted that databases and/or additional components may be utilized with, or integrated into, any type of network element coupled to the networks 104, 106, 108. In the context of the present description, a network element may refer to any component of a network.

According to some approaches, methods and systems described herein may be implemented with and/or on virtual systems and/or systems which emulate one or more other systems, such as a UNIX system which emulates an IBM z/OS environment, a UNIX system which virtually hosts a MICROSOFT WINDOWS environment, a MICROSOFT WINDOWS system which emulates an IBM z/OS environment, etc. This virtualization and/or emulation may be enhanced through the use of VMWARE software, in some embodiments.

In more approaches, one or more networks 104, 106, 108, may represent a cluster of systems commonly referred to as a "cloud." In cloud computing, shared resources, such as processing power, peripherals, software, data, servers, etc., are provided to any system in the cloud in an on-demand relationship, thereby allowing access and distribution of services across many computing systems. Cloud computing typically involves an Internet connection between the systems operating in the cloud, but other techniques of connecting the systems may also be used.

Figure 2:
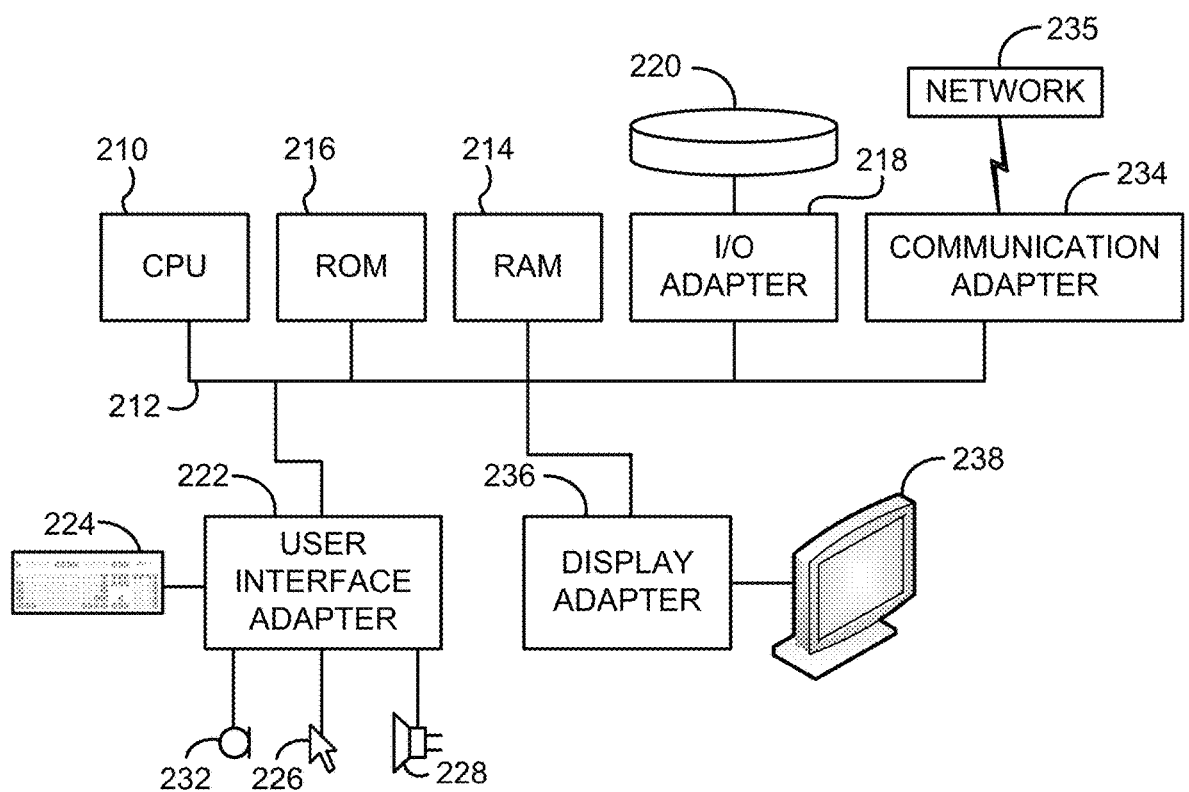
FIG. 2 is a representative hardware environment that may be associated with the servers and/or clients of FIG. 1, in accordance with one embodiment.

FIG. 2 shows a representative hardware environment associated with a user device 116 and/or server 114 of FIG. 1, in accordance with one embodiment. Such figure illustrates a typical hardware configuration of a workstation having a central processing unit 210, such as a microprocessor, and a number of other units interconnected via a system bus 212.

The workstation shown in FIG. 2 includes a Random Access Memory (RAM) 214, Read Only Memory (ROM) 216, an input/output (I/O) adapter 218 for connecting peripheral devices such as disk storage units 220 to the bus 212, a user interface adapter 222 for connecting a keyboard 224, a mouse 226, a speaker 228, a microphone 232, and/or other user interface devices such as a touch screen and a digital camera (not shown) to the bus 212, communication adapter 234 for connecting the workstation to a communication network 235 (e.g., a data processing network) and a display adapter 236 for connecting the bus 212 to a display device 238.

The workstation may have resident thereon an operating system such as the Microsoft Windows® Operating System (OS), a MAC OS, a UNIX OS, etc. It will be appreciated that a preferred embodiment may also be implemented on platforms and operating systems other than those mentioned. A preferred embodiment may be written using eXtensible Markup Language (XML), C, and/or C++ language, or other programming languages, along with an object oriented programming methodology. Object oriented programming (OOP), which has become increasingly used to develop complex applications, may be used.

As mentioned above, various embodiments described herein provide predictive fall prevention using corrective sensory stimulation induced intervention. Falls are the leading cause of injury and the most common cause of non-fatal trauma-related hospital admissions among older adults. It has been estimated that falls result in more than 2.8 million injuries treated in emergency departments annually, including over 800,000 hospitalizations.

The majority of such fall-related injuries are caused by obstacles, e.g., potholes, liquid, objects, etc., residing within the walking path of the victim of the fall. For example, such obstacles may cause a user to fall as a result of the user, e.g., slipping on an obstacle, tripping over an obstacle, stepping into an obstacle, etc. Conventional efforts taken to mitigate such dangerous obstacles include canes and/or walker assisting devices. These conventional efforts however are often unable to assist users in recognizing obstacles within a walking direction and/or assisting users beyond offering minimal physical support to lean against. These conventional canes/walker assisting devices moreover are unattractive to many users, and bulky.

Various embodiments and approaches herein implement corrective sensory stimulations for prompting a user to not contact detected obstacles that might otherwise have caused the user to fall as a result of contacting such obstacles.

Figure 3:
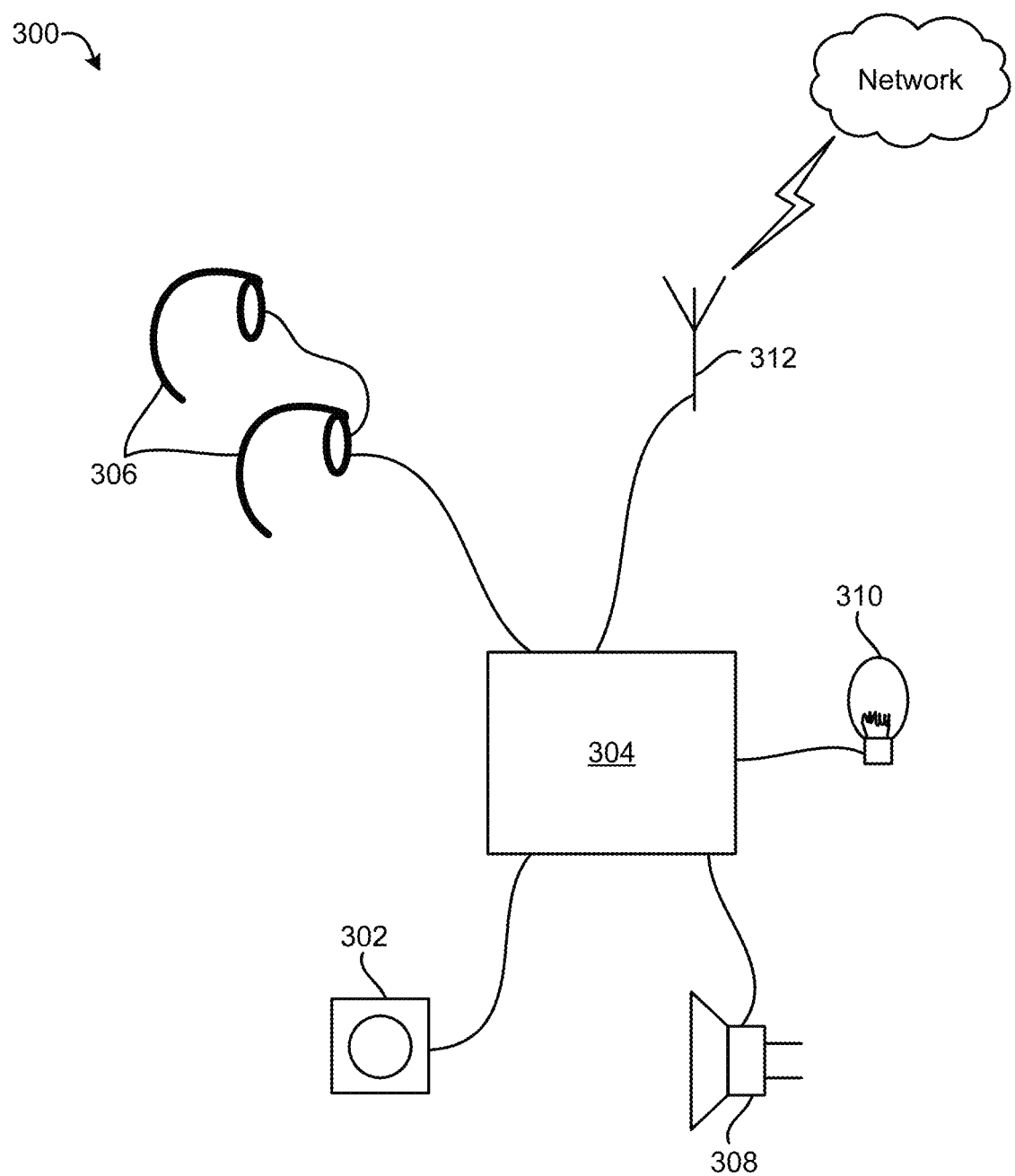
FIG. 3 is a view of an apparatus for predictive fall prevention, in accordance with one embodiment.

Now referring to FIG. 3, an apparatus 300, such as a computer, for predictive fall prevention is shown according to one embodiment. Note that some of the elements shown in FIG. 3 may be implemented as hardware and/or software, according to various embodiments.

FIG. 3 depicts the apparatus 300, in accordance with one embodiment. As an option, the present apparatus 300 may be implemented in conjunction with features from any other embodiment listed herein, such as those described with reference to the other FIGS. Of course, however, such apparatus 300 and others presented herein may be used in various applications and/or in permutations which may or may not be specifically described in the illustrative embodiments listed herein. Further, the apparatus 300 presented herein may be used in any desired environment.

Apparatus 300 includes a camera 302 for capturing image data of a survey area of a surface in a direction of travel of a user. Accordingly, the camera may be worn by the user, as will be described in greater detail elsewhere herein.

A processor 304 is coupled to the camera 302 for analyzing the image data for determining whether an obstacle is present in the survey area of the surface, and within a predetermined distance of the user. According to various approaches, the image data may include any of, e.g., a partial picture, a single picture, a plurality of pictures (such as a video), etc.

As will also be described in greater detail elsewhere herein, in response to determining an obstacle is present in the survey area of the surface within a predetermined distance of the user, the processor outputs an instruction to apply a corrective sensory stimulation for offsetting balance of the user in a direction away from the obstacle. The instruction is received by at least one sensory user device coupled to the processor for applying the corrective sensory stimulation to the user in response to receiving the instruction. In apparatus 300, the sensory user device includes at least a galvanic vestibular stimulation device 306. The galvanic vestibular stimulation device 306 is preferably worn close to and/or within the user's ears. The galvanic vestibular stimulation device in the embodiment shown includes two ear-borne transmitters having a shape like ear buds. In various approaches, the ear-borne transmitters can be in the form of a galvanic vestibular stimulation enabled headphone having a similar shape as conventional over-ear or on-ear headphones, ear buds, etc.

Moreover, in the present approach, the sensory user device additionally and/or alternatively includes a speaker 308 and/or a light 310. For example, the speaker may be in each earpiece of the aforementioned headphone. Moreover, apparatus 300 may include an antenna 312 which is in communication with a network, e.g., for accessing storage and/or other similar apparatuses.

It should be noted that depending on the approach, some or all of the components of the apparatus 300 are physically coupled together. In other approaches, some or all of the components are not physically coupled with other components of the apparatus 300. In such approaches, the components that are not physically coupled to any other component of the apparatus 300 are indirectly coupled, e.g., wireless coupling, to other components of the apparatus 300.

Figure 4:
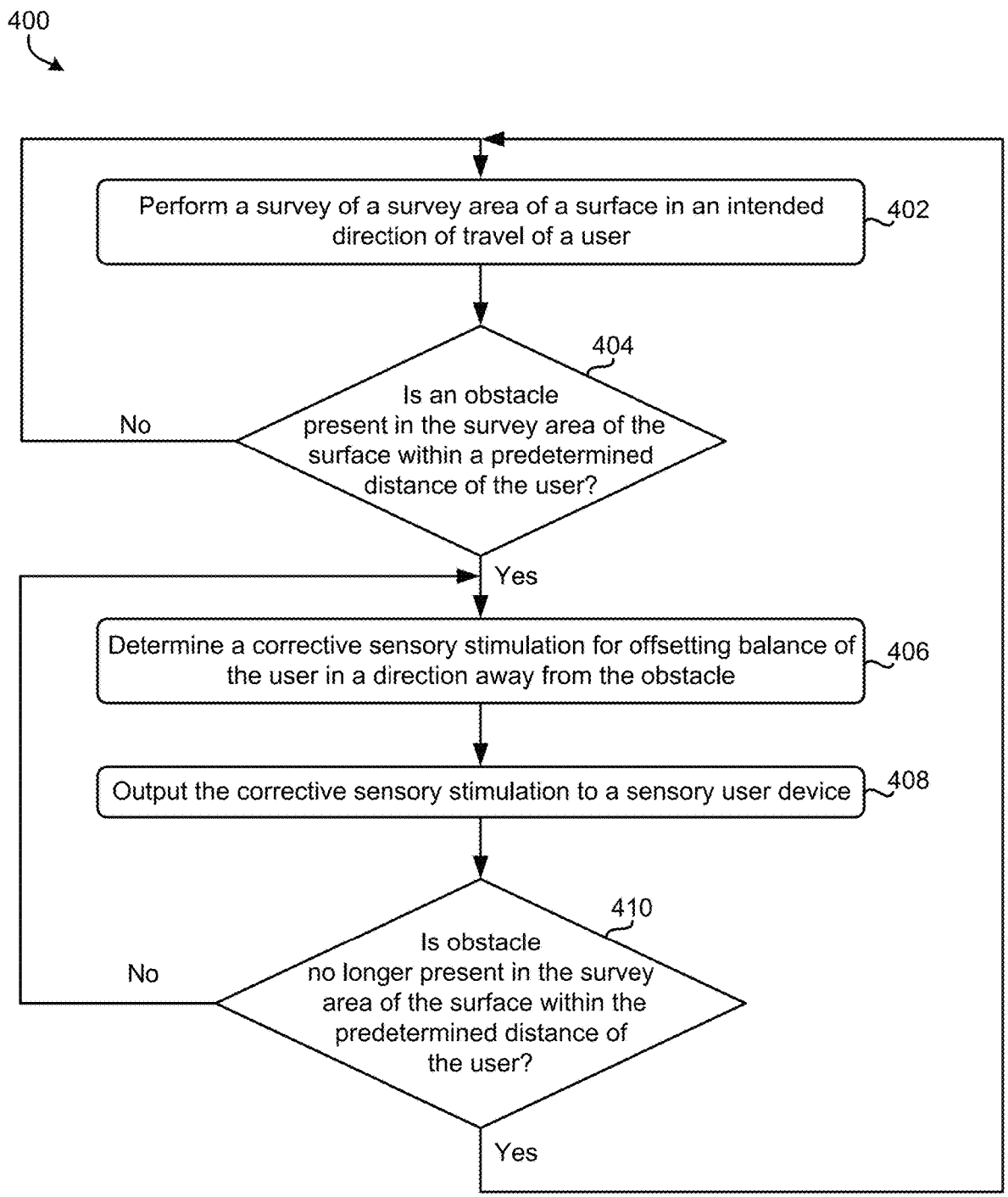
FIG. 4 is a flowchart of a method, according to one embodiment.

Now referring to FIG. 4, a flowchart of a method 400 is shown according to one embodiment. The method 400 may be performed in accordance with the present invention in any of the environments depicted in FIGS. 1-3 and 5A-6B, among others, in various embodiments. Of course, more or less operations than those specifically described in FIG. 1 may be included in method 400, as would be understood by one of skill in the art upon reading the present descriptions.

Each of the steps of the method 400 may be performed by any suitable component of the operating environment. For example, in various embodiments, the method 400 may be partially or entirely performed by a computer, or some other device having one or more processors therein. The processor, e.g., processing circuit(s), chip(s), and/or module(s) implemented in hardware and/or software, and preferably having at least one hardware component may be utilized in any device to perform one or more steps of the method 400. Illustrative processors include, but are not limited to, a central processing unit (CPU), an application specific integrated circuit (ASIC), a field programmable gate array (FPGA), etc., combinations thereof, or any other suitable computing device known in the art.

Of course, this logic may be implemented as a method on any device and/or system or as a computer program product, according to various embodiments.

Operation 402 of method 400 includes performing a survey of a survey area of a surface in an intended direction of travel of a user. According to various approaches, the survey area of the surface considers a portion of any known type of surface that humans walk on, e.g., sidewalks, outdoor trails, indoor hallways, etc.

The survey area of the surface includes any amount of area, and is adjustable at any time for any reason. For example, the survey area of the surface may become larger than a most previous survey area in response to detecting and/or receiving an indication that the user is moving relatively quickly, e.g., running, jogging, walking briskly, etc. In another example, the survey area of the surface may become smaller than a most previous survey area in response to detecting and/or receiving an indication that the user is moving relatively slowly and/or stopped, e.g., walking, limping, stationary, etc.

In preferred approaches, the survey is performed using a surface monitoring wearable camera. More specifically, the survey area is at least a portion of a field of view of a camera. For example, in one approach the camera is mounted to a user's clothing, e.g., such as about the chest region of a user's shirt. In another approach, the camera is attached to and/or integrated with eyewear of a user. Such a camera location is particularly useful for users that already wear glasses of any kind. In yet another approach, the camera is mounted and/or integrated with a user's belt or any other waist mounted utility. In a further approach, the camera is attached to and/or integrated with the galvanic vestibular stimulation device, e.g., the camera is coupled to one of the ear-mounted transmitters. Note that the aforementioned locations for mounting the surface monitoring wearable camera position the field of view of the camera in an intended direction of travel of the user, e.g., assuming that the user is walking in a foreword manner.

Decision 404 of method 400 includes determining whether an obstacle is present in the survey area of the surface within a predetermined distance of the user. Conventional image recognition software may be used for determining whether obstacles are present in image data of the survey area obtained by the camera. Accordingly, decision 404 of method 400 includes performing recognition of any type of obstacle, e.g., a hole, an object protruding or extending above the surface within the survey area, a cord, a stair, a slope, a liquid and/or any other slippery surface, etc. Optionally, the actual type of obstacle can be identified.

Determining whether the obstacle is within the predetermined distance may include use of conventional range finder technology for determining the distance of the obstacle, which distance is compared to the predetermined distance. The predetermined distance is preferably a distance that allows adequate time to administer corrective action to a user before the user contacts the obstacle. The predetermined distance may be a preset number, a dynamic value that changes with user speed, etc. In some approaches, the predetermined distance may be equal to about an average stride length of the user.

In one approach, in response to determining that a detected obstacle is present in the survey area of the surface within the predetermined distance of the user (e.g., as illustrated by the "Yes" logical path of decision 404) a process is performed as will now be described. It should be prefaced that the process preferably includes performing operations 406-408. As will be understood by one of ordinary skill in the art upon reading the descriptions herein, the process is performed to prevent the user from contacting the detected obstacle, because otherwise contacting the obstacle could potentially cause the user to fall and be injured.

Operation 406 includes determining a corrective sensory stimulation for offsetting balance of the user in a direction away from the obstacle. The selected corrective sensory stimulation may simply be the default corrective sensory stimulation set for the particular user, and therefore, operation 406 merely includes selecting the default corrective sensory stimulation. In other approaches, the type of corrective sensory stimulation may be selected from a set of types. In yet other approaches, the corrective sensory stimulation may be computed based on factors, such as one or more of: speed of travel of the user, position of the obstacle relative to the user's position and/or trajectory, etc.

According to various approaches, the corrective sensory stimulation includes any known type of stimulation. In preferred approaches, the corrective sensory stimulation is galvanic vestibular and/or neuromuscular stimulation.

In other approaches, the corrective sensory stimulation additionally and/or alternatively includes any one or more of, e.g., an audible tone/message, a sensory indicator such as a vibration, a visual indicator, etc.

The corrective sensory stimulation is output to a sensory user device, e.g., see operation 408. According to various approaches, the sensory user device includes any type of device that is configured to, e.g., play, administer, broadcast, etc., the determined corrective sensory stimulation.

In one approach, the sensory user device includes a galvanic vestibular stimulation enabled headphone. As will be understood by one of ordinary skill in the art upon reading the descriptions herein, galvanic vestibular stimulation enabled headphones are particularly useful for users that have diminished eyesight and/or hearing capabilities. This is because assuming that the user is wearing the sensory user device, the user will experience the corrective sensory stimulation, and thereby be physically discouraged from contacting and/or be alerted of the obstacle.

In preferred approaches, the corrective sensory stimulation includes a vestibular stimulation that offsets balance of the user in a direction away from the obstacle. In some approaches, such stimulation includes and/or is supplemented with a known type of neuromuscular stimulation. As a result, the user will be at least temporarily physically imbalanced, and the user's subsequent instinctive counterbalancing will divert the user from contacting the obstacle (which would have otherwise potentially resulted in the user falling). For example, galvanic vestibular stimulation includes small electric stimuli on the vestibular system in the user's inner ear. As a result of experiencing the small electric stimuli, the user perceives a sensation of rolling away from a direction defined by the type of stimuli applied. This phenomenon can be used to create the sensation of rolling in a direction away from the obstacle, whereby the user attempts to counterbalance in response to the stimuli, thereby moving away from the obstacle or at least stopping. For example, assume that a user is one stride from contacting an obstacle. Preferred stimuli in such an example would cause the user (that experiences the corrective sensory stimulation from a sensory user device that the user is wearing) to feel as if the user is rolling backward away from the obstacle. Accordingly, the user instinctively takes an action to counterbalance the feeling that the user was falling backward, such as taking a step backward, in a safe direction away from the obstacle. Of course, the direction that the stimuli causes the user to feel that the user is rolling depends on the relative location of the obstacle with respect to the user. For example, an obstacle that is forty-five degrees off of a user's intended direction of travel will correspond to different stimuli than the stimuli discussed in the example above having an obstacle directly in front of the user. Specifically, in some approaches, the specific ear(s), e.g., right ear and/or left ear, to which the stimuli are output to and/or the relative degree of stimuli applied to a particular ear may be different for positioning of obstacle(s) with respect to the user.

Accordingly, the user does not need to identify such obstacles at any point in time. Instead, various operations and/or decisions of method 400 include determining such obstacles for the user, and determining a corrective mitigation strategy for assisting the user in avoiding such obstacles.

It should be noted that such a stimulation preferably gently offsets the balance of the user to a degree that causes the user to resist taking another step forward. This reminds the user to survey the surface that the user was about to contact (potentially identifying obstacles thereon), and select an alternative route that does not include contacting the obstacle.

Using sensory stimulation, and more particularly vestibular stimulation as the determined corrective sensory stimulation is preferred because according to some studies the average reaction time of humans to vestibular samples is about 55-60 milliseconds (ms). Such reaction times should be considered in view of the relatively longer average reaction time of humans to audio samples which is about 260 ms, and the relatively longer average reaction time of humans to visual samples which is about 340 ms. However, although the corrective sensory stimulation such as vestibular stimulation is the preferred output for ensuring that the user does not contact the obstacle, in some approaches, as mentioned elsewhere above, method 400 additionally and/or alternatively include outputting other warnings of the obstacle to the user. For example, in one approach, the corrective sensory stimulation is output with an audio and/or visual warning of the obstacle to the sensory user device. In such an approach, the audio and/or visual warning of the obstacle may include any one or more of, e.g., a broadcasted warning message, a pulsing and/or illumination of one or more lights of the sensory user device, a calibrated vibration of the sensory user device, etc.

In the method 400, the corrective sensory stimulation and/or any other warning of the determined obstacle are output based on a position of the user with respect to the obstacle, namely, when the obstacle is within the predetermined distance. For example, in one preferred approach, the corrective sensory stimulation is output when the user is positioned about one average stride of the user from contacting the obstacle. According to various approaches, the average stride is determined from collected user data, e.g., average walking speed, stride length, user height, etc.

Outputting the corrective sensory stimulation when the user is positioned about one average stride of the user from contacting the obstacle in most cases results in the user avoiding contact with the obstacle completely. However, in other approaches, the corrective sensory stimulation is output when the user is positioned any predetermined distance from the obstacle.

It should be noted that users each typically have different physical statures, and therefore, in some approaches, the amount of corrective sensory stimulation output is determined based at least in part on at least one user trait. For example, according to various approaches, the amount of corrective sensory stimulation output is determined based at least in part on at least one user trait, e.g., an average stride distance of the user, a body weight of the user, a height of the user, a walking speed of the user, an age of the user, etc. Accordingly, the amount of corrective sensory stimulation output will relatively lower for a user having relatively smaller user traits, e.g., shorter, lighter, slower, etc. than for a user having relatively greater user traits. This determination of operation 406 is important because smaller users might otherwise fall down as a result of experiencing too great of a corrective sensory stimulation.

It should be noted that although the output sensory stimulation will likely result in the user not contacting the obstacle, in some approaches, more than a single iteration of the process is performed. For example, in one approach, the process is performed until it is determined that the obstacle is not present in the survey area of the surface within the predetermined distance of the user. Accordingly, decision 410 of method 400 includes determining if the obstacle is no longer present in the survey area of the surface within the predetermined distance of the user.

In one approach, in response to determining that the obstacle is no longer present in the survey area of the surface within the predetermined distance of the user (e.g., as illustrated by the "Yes" logical path of decision 410) the method 400 returns to operation 402. Moreover, in another approach, in response to determining that the obstacle is still present in the survey area of the surface within the predetermined distance of the user (e.g., as illustrated by the "No" logical path of decision 410) the process, e.g., operations 406-408, are performed.

With reference again to the survey performed in operation 402, it should be noted that in some approaches, it is determined from a survey that an obstacle is present in the survey area of the surface outside of, e.g., beyond, the predetermined distance of the user. Although such an obstacle is not at the time the survey is performed an immediate threat to the user's stability, an optional operation of method 400 includes performing another survey of the surface, e.g., after a predetermined amount of time has elapsed, in response to detecting that the user has performed a predetermined number of steps, in response to determining that the user's rate of movement has increased and/or decreased, etc. The subsequent survey provides an updated surveying to determine whether the obstacle that was previously determined to be in the survey area of the surface outside of the predetermined distance of the user, is now in the survey area of the surface within the predetermined distance of the user. Accordingly, the predetermined amount of time is preferably short enough to provide adequate monitoring to prevent the user from encountering the obstacle. The predetermined amount of time may be a default value, a value set by the user, may vary based on a speed of the user (e.g., decrease as the user speed increases), etc.

In one approach, the subsequent survey considers at least the previous detection of the obstacle. In such an approach, consideration of the previous detection of the obstacle is used for any one or more determinations, e.g., for determining whether the user is directionally heading toward the obstacle, for determining the rate at which the user is advancing toward the obstacle, for determining the intended direction of travel of a user, etc.

It should be noted that any determining of method 400 may be stored and/or output (e.g., see storage of FIG. 3) with an associated geographical location at which the obstacle exists for future reference. Moreover, the path that a user is influenced to take as a result of the outputting may additionally and/or alternatively be stored and/or output. Any of such information may be subsequently accessed, e.g., for use by the same user when the user is again using the sensory user device and walking on the surface, for use by another user that is using a similar sensory user device and that is walking on the surface, for generating user behavior traits that subsequently determined corrective sensory stimulations are at least in part based on, etc.

Figure 5A:
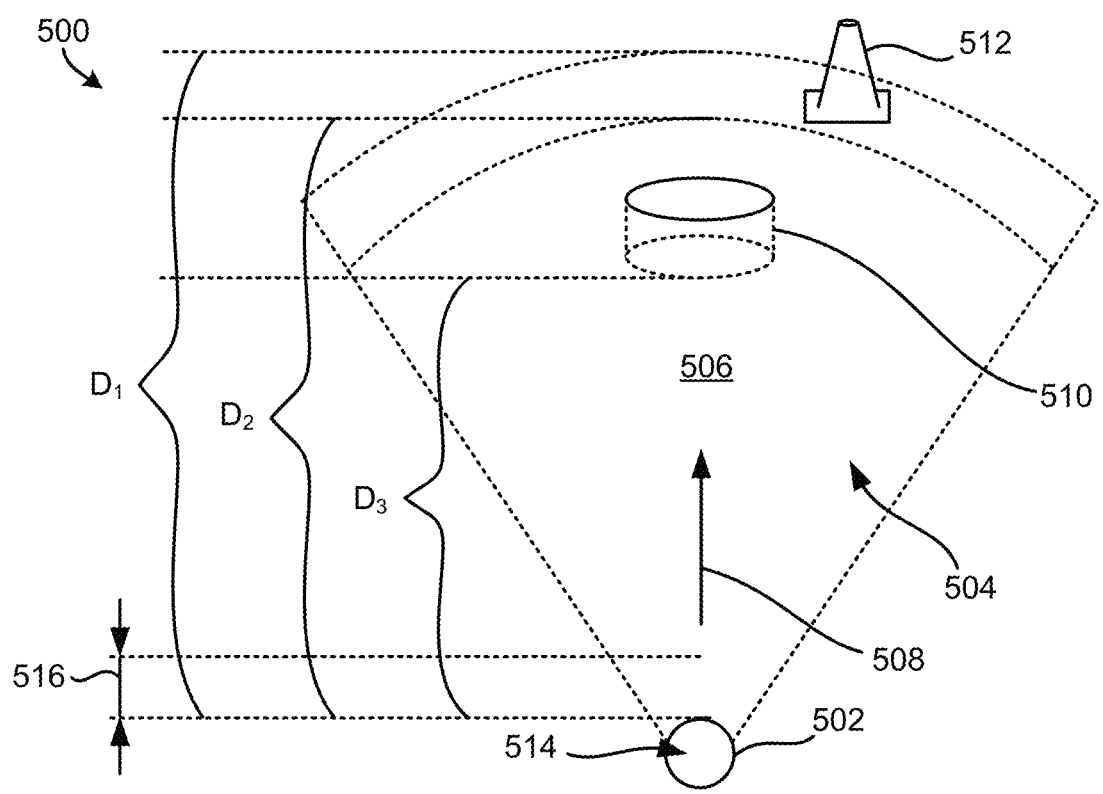
FIG. 5A is an overview of an environment having a user walking in an intended direction of travel across a surface having a plurality of obstacles.
Figure 5B:
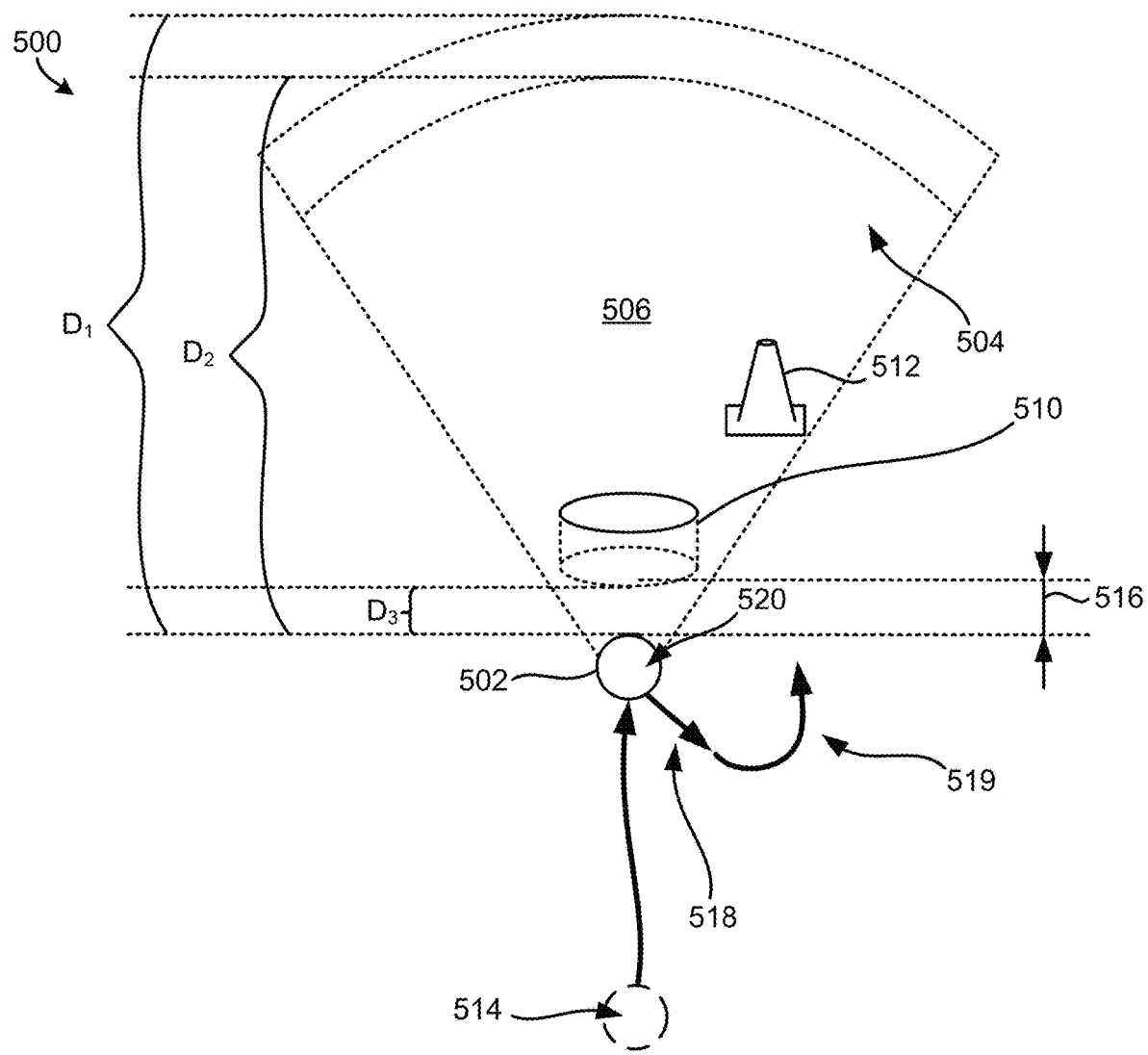
FIG. 5B is an overview of the environment of FIG. 5A.
Figure 5C:
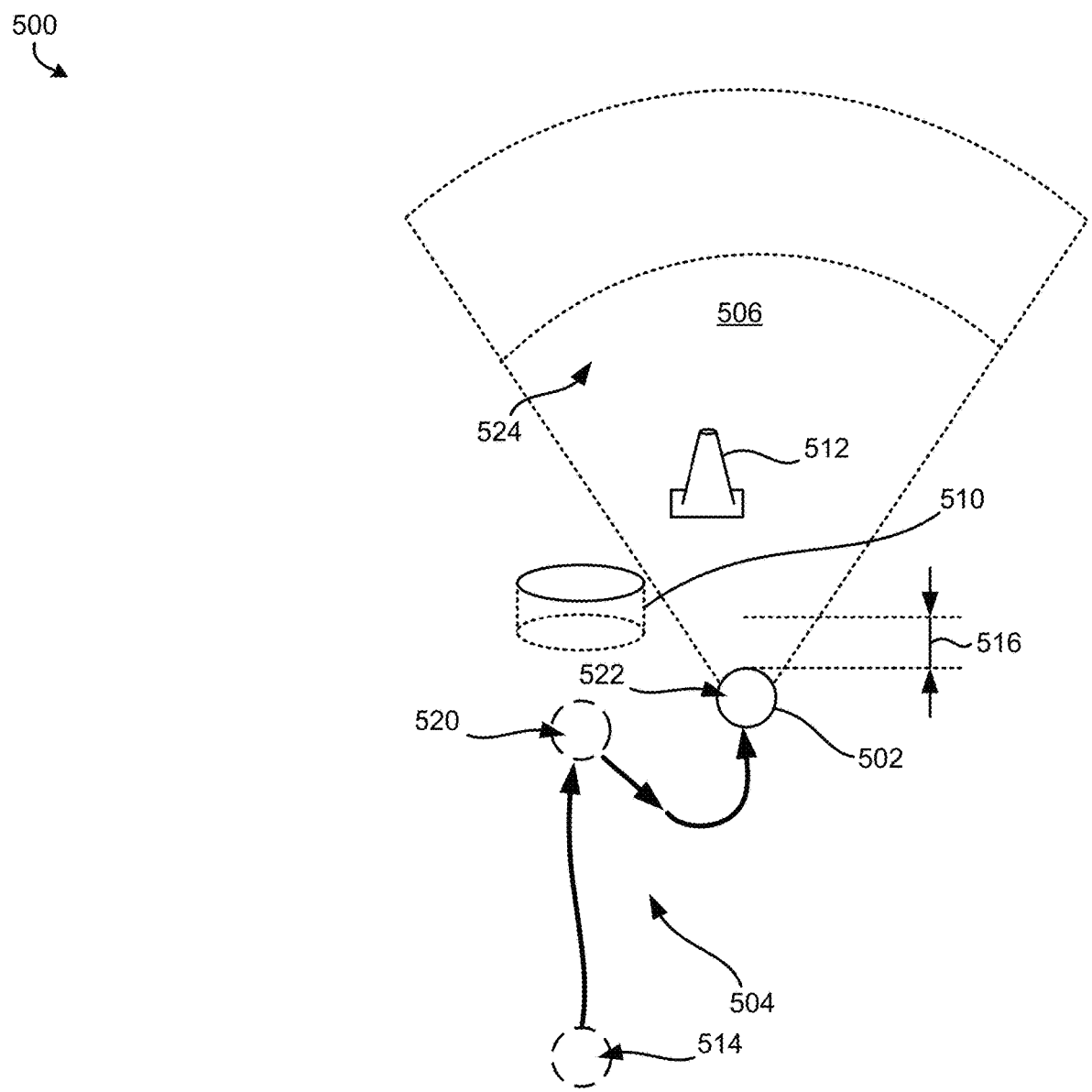
FIG. 5C is an overview of the environment of FIGS. 5A-5B.

FIGS. 5A-5C depicts an environment 500, in accordance with one embodiment. As an option, the present environment 500 may be implemented in conjunction with features from any other embodiment listed herein, such as those described with reference to the other FIGS. Of course, however, such environment 500 and others presented herein may be used in various applications and/or in permutations which may or may not be specifically described in the illustrative embodiments listed herein. Further, the environment 500 presented herein may be used in any desired environment.

For reference, FIGS. 5A-5C specifically depict, according to one example, how a user is prevented from contacting various obstacles (which otherwise would have likely result in the user falling), as a result of various embodiments and/or approaches described elsewhere herein being performed, e.g., see method 400.

With reference now to FIG. 5A, environment 500 includes a user 502 moving in an intended direction of travel 508 along a surface 506. The user 502 is shown at least initially positioned in a first location 514.

A survey has been performed of a survey area 504 in the intended direction of travel 508 of the user 502. In the present approach, the survey has a circumferential bound of $D_1$ within the survey area 504.

In the present approach, it is determined from the survey that the survey area 504 includes two obstacles, e.g., a first obstacle 510 and a second obstacle 512. The first obstacle 510 is present in the survey area 504 of the surface within an area of interest of the user 502, e.g., the area of interest is a portion of the survey area 504 that is located less than or equal to a distance $D_2$ from the user 502 when the survey is performed. Note that in some approaches, the survey area and the area of interest are the same, e.g., $D_1$ equals $D_2$.

In the example shown, the second obstacle 512 resides in the survey area 504 of the surface outside of the area of interest. The first obstacle 510 resides in the area of interest but outside the predetermined distance 516 that is indicative of imminent contact e.g., a distance $D_3$ between the obstacle 510 and the user is greater than the predetermined distance 516.

According to one approach, the area of interest includes at least a portion of the survey area 504 that is readily accessible to the user 502, based at least in part on the current rate of travel of the user 502. To clarify, in the present approach the area of interest being a readily accessible portion of the survey area 504 corresponds to locations of the survey area 504 that are accessible to the user within a predetermined amount of time (based on the user's current rate of travel), e.g., three seconds, five seconds, ten seconds, etc. The predetermined amount of time is preferably at least the sum of: an amount of time that allows the user to be administered a corrective sensory stimulation, an amount of time that allows the user to acknowledge the corrective sensory stimulation (at least about 55-60 milliseconds), and an amount of time that allows the user to perform counterbalance of the corrective sensory stimulation. Moreover, the predetermined amount of time is subject to change in accordance with the rate of travel of the user changing, e.g., outermost bounds of the area of interest expand as the rate of travel of the user increases. Because obstacles that reside within the area of interest are readily accessible to the user 502, as defined by the current rate of travel of the user, in one approach, processing performed for facilitating user avoidance of obstacles within the area of interest are awarded a higher priority than any obstacles that are outside of the area of interest. For example, a device performing various operations and/or determinations for assisting the user in avoiding the obstacles 510, places such processing at a higher priority than processing performed for avoiding the obstacles 512. In some approaches, this assignment of processing priority preserves processing potential for other tasks that have also been awarded a higher priority than any obstacles that are outside of the area of interest. For example, assume that ten obstacles reside outside of the area of interest and a single obstacle resides within the area of interest. In such an example, processing performed that is related to user avoidance of the obstacle within the area of interest is awarded a large amount of processing resources. Meanwhile, processing performed that is related to user avoidance of the obstacles outside of the area of interest are awarded only minimal processing resources. Accordingly, the remaining preserved processing resources (if any) remain available for other urgent tasks.

Referring now to FIG. 5B, note that the user 502 has advanced to a second location 520 adjacent the first obstacle 510 which is present in the survey area 504 of the surface 506 within the predetermined distance 516 of the user 502, e.g., note that the distance $D_3$ between the obstacle 510 and the user is less than the predetermined distance 516. In the present approach the predetermined distance 516 is about one average stride of the user from contacting the obstacle 510, but again, can be any predefined value. Accordingly, in the present approach, during another survey, the obstacle 510 is determined to be present in the survey area 504 of the surface 506 within the predetermined distance 516 of the user 502, in response to which a process is performed until it is determined that the obstacle 510 is not present in the survey area 504 of the surface within the predetermined distance 516 of the user 502. In the present approach, the process includes determining a corrective sensory stimulation for offsetting balance of the user 502 in a direction away from the obstacle 510. Moreover, the process includes outputting the corrective sensory stimulation to a sensory user device (that the user is assumed to be wearing in the present approach). As described elsewhere herein, as a result of experiencing the corrective sensory stimulation, the user's balance will be offset, and the user will be influenced to counterbalance in a direction away from the obstacle. For example, in the present approach, as a result of experiencing the corrective sensory stimulation, the user's instinctive counterbalance diverts the user along the direction 518, e.g., by applying more stimulation to one side of the user's head than the other. Now alerted to the presence of the obstacle 510, and having avoided contact therewith, the user proceeds along direction 519.

Referring now to FIG. 5C, the user is shown at a third location 522, e.g., as a result of experiencing the corrective sensory stimulation and subsequent repositioning in FIG. 5B along the direction 518. As previously mentioned, when the survey was initially performed, the second obstacle 512 resided in the survey area 504 of the surface 506 outside of the predetermined distance 516 of the user 502. The second obstacle 512 also resided in the survey area 504 of the surface 506 outside of the predetermined distance 516 of the user 502. In the third location 522, another survey is performed, e.g., as a result of determining that the location of the user 502 has changed, in response to a predetermined amount of time has elapsed, in response to outputting corrective sensory stimulation, etc. The current survey has a survey area 524. The current survey considers at least the previous detection of the obstacle 512 that was previously determined (in the initial survey) to reside in the survey area 504 of the surface 506 outside of the predetermined distance 516 of the user 502. In some approaches, the current survey additionally and/or alternatively considers any other previously detected obstacle, e.g., the first obstacle 510.

With the detected second obstacle 512 determined, various operations similar to those described above are performed for preventing the user from contacting the second obstacle 512, e.g., once it is determined that the obstacle 512 is within the predetermined distance 516 of the user 502. Note that in FIG. 5C, the obstacle 512 is outside of the predetermined distance 516 of the user 502.

It should be assumed that the user 502 has a slower rate of travel at the third location 522 than the user's previous rate of travel at the first location 514, e.g., the user moved relatively slower while counterbalancing himself/herself along the direction 518 into the third location 522. Accordingly, an area of interest of the current survey is spatially smaller than the area of interest of the initial survey.

Figure 6A:
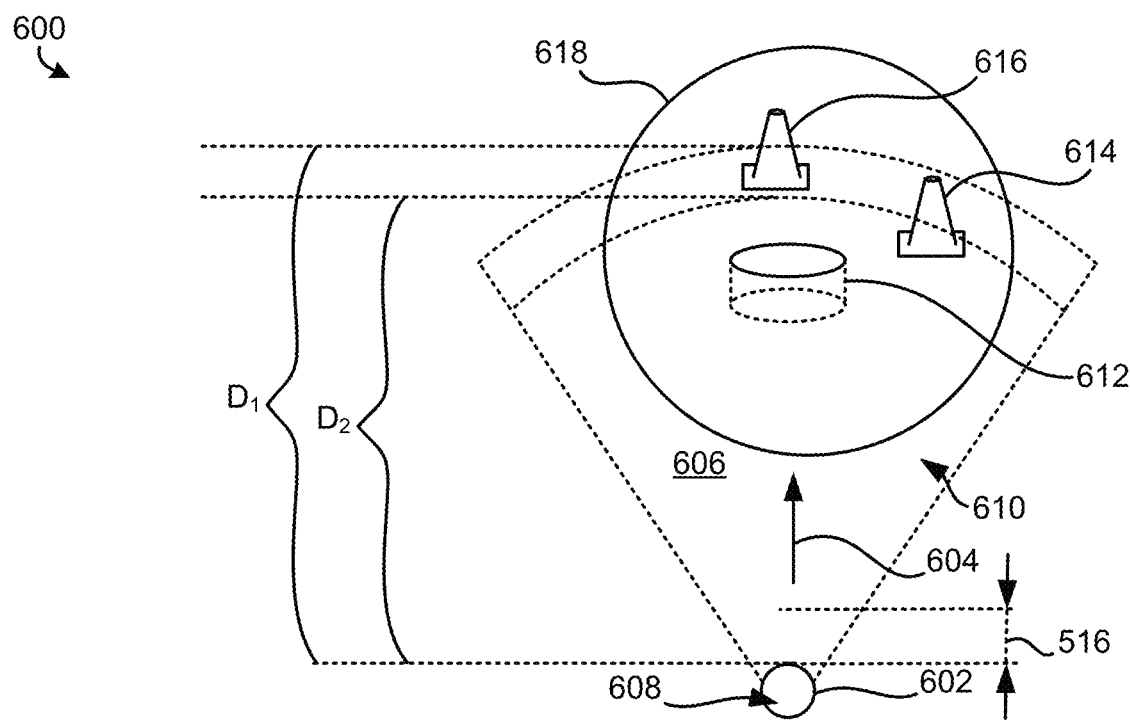
FIG. 6A is an overview of an environment having a user walking in an intended direction of travel across a surface having a plurality of obstacles.
Figure 6B:
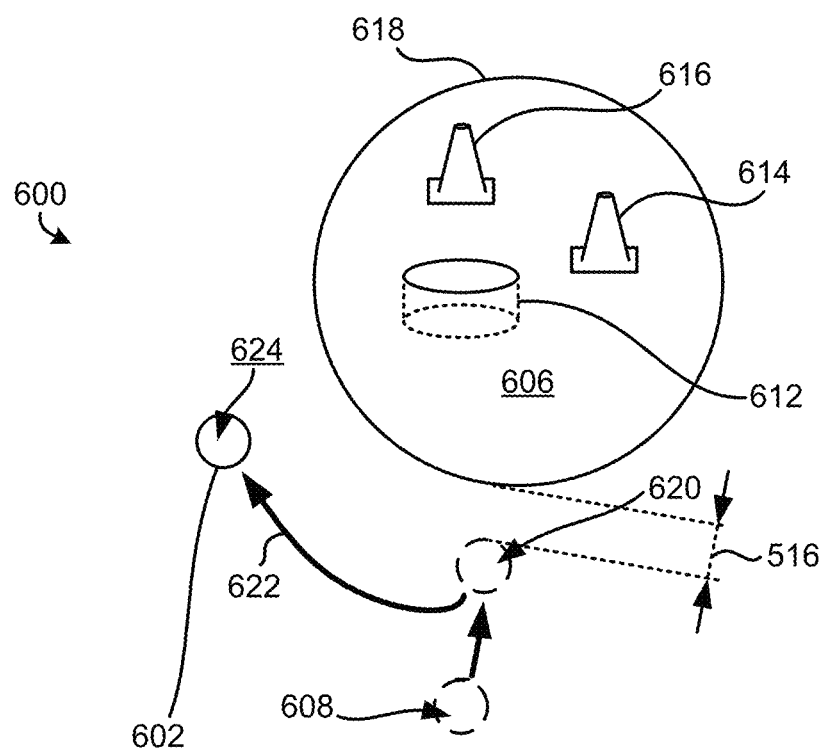
FIG. 6B is an overview of the environment of FIG. 6A.

FIGS. 6A-6B depicts an environment 600, in accordance with one embodiment. As an option, the present environment 600 may be implemented in conjunction with features from any other embodiment listed herein, such as those described with reference to the other FIGS. Of course, however, such environment 600 and others presented herein may be used in various applications and/or in permutations which may or may not be specifically described in the illustrative embodiments listed herein. Further, the environment 600 presented herein may be used in any desired environment.

Similar to FIGS. 5A-5C, FIGS. 6A-6B depict, according to one example, a user that is influenced to not contact various obstacles (which otherwise would have likely resulted in the user falling), as a result of various embodiments and/or approaches described elsewhere herein being performed, e.g., see method 400. It should be noted that various similar illustrations of the environments 500, 600 may share common numberings.

With reference now to FIG. 6A, environment 600 includes a user 602 having an intended direction of travel 604 along a surface 606. The user 602 is shown at least temporarily positioned in a first location 608.

A survey has been performed of a survey area 610 in the intended direction of travel 604 of the user 602. In the present approach, the survey has a circumferential bound of $D_1$ within the survey area 610.

In the present approach, it is determined from the survey that the survey area 610 includes a plurality of obstacles, e.g., a first obstacle 612, a second obstacle 512, and a third obstacle 616. The first obstacle 612 and the second obstacle 614 are determined to be present in an area of interest, e.g., the area of interest is a portion of the survey area 610 that is located less than or equal to a distance $D_2$ from the user 502 when the survey is performed. The third obstacle 616 is determined to reside in the survey area 610 of the surface 606 outside of the area of interest. Moreover, each of the obstacles reside outside of a predetermined distance 516 of the user 602.

In one approach, the plurality of obstacles 612-618 are grouped together as a group of obstacles 618, e.g., defined by a computer-generated perimeter surrounding the obstacles 612, 614, 616 in the present approach. The perimeter may extend along outer surfaces of the obstacles, or may be set a predetermined distance away from the obstacles, as shown. In various approaches herein, a group of obstacles may be characterized by a plurality of obstacles that are present in the survey area of the surface, where each of the obstacles are determined to be within a predetermined distance from another one of the obstacles. According to various approaches, the predetermined distance includes any amount of distance that may be adjusted for any reason. Moreover, the predetermined distance is based on any one or more of, e.g., a determined type of obstacle, a distance of the user to the closest obstacle, the rate of travel of the user, etc.

In some approaches, it is beneficial to determine a single corrective sensory stimulation for offsetting balance of the user in a direction away from a perimeter of a group of obstacles, rather than determining a series of corrective sensory stimulations for offsetting balance of the user in a direction away from each obstacle individually, e.g., upon the user 602 coming within the predetermined distance 516 of each of the obstacles. For example, such benefits include, e.g., less sensory stimulation experienced by the user, a more quickly established intended direction of travel for the user that avoids all of the obstacles determined to be present in the survey area of the surface, less processing performed by the one or more devices that are performing corrective sensory stimulation determinations, etc.

A corrective sensory stimulation for offsetting balance of the user in a direction away from the group of obstacles 618 is determined in response to determining that the perimeter of the group of obstacles 618 is located less than or equal to the predetermined distance 516 from the user 602, e.g., see FIG. 6B. For example, referring now to FIG. 6B, a second location 620 of the user 602 is illustrated according to one approach. At the second location 620 the user 602 is about one average stride of the user 602 from trespassing the perimeter of the group of obstacles 618. Accordingly, the corrective sensory stimulation is output to a sensory user device worn by the user (not shown). As a result of experiencing the corrective sensory stimulation, the user's balance is offset, thereby causing the user to not contact the any of the obstacles 612-616, nor trespass the perimeter of the group of obstacles 618. Rather, in the current example the user's subsequent instinctive counterbalance diverts the user along a direction 622 to a third location 624, away from the group of obstacles 618.

Grouping a plurality of obstacles may be useful where the surface that a user is walking on contains numerous obstacles, e.g., such as at a sporting events with numerous cones, poor sections of a walkway that include numerous potholes, an indoor event that includes numerous ground wire paths traversing a walkway, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN, or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Moreover, a system according to various embodiments may include a processor and logic integrated with and/or executable by the processor, the logic being configured to perform one or more of the process steps recited herein. The processor may be of any configuration as described herein, such as a discrete processor or a processing circuit that includes many components such as processing hardware, memory, I/O interfaces, etc. By integrated with, what is meant is that the processor has logic embedded therewith as hardware logic, such as an application specific integrated circuit (ASIC), a FPGA, etc. By executable by the processor, what is meant is that the logic is hardware logic; software logic such as firmware, part of an operating system, part of an application program; etc., or some combination of hardware and software logic that is accessible by the processor and configured to cause the processor to perform some functionality upon execution by the processor. Software logic may be stored on local and/or remote memory of any memory type, as known in the art. Any processor known in the art may be used, such as a software processor module and/or a hardware processor such as an ASIC, a FPGA, a central processing unit (CPU), an integrated circuit (IC), a graphics processing unit (GPU), etc.

It will be clear that the various features of the foregoing systems and/or methodologies may be combined in any way, creating a plurality of combinations from the descriptions presented above.

It will be further appreciated that embodiments of the present invention may be provided in the form of a service deployed on behalf of a customer to offer service on demand.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A computer-implemented method, comprising:
   performing a survey of a survey area of a surface in an intended direction of travel of a user;
   determining whether an obstacle is present in the survey area of the surface within a predetermined distance of the user;
   in response to determining that an obstacle is present in the survey area of the surface within the predetermined distance of the user, performing the following process until it is determined that the obstacle is not present in the survey area of the surface within the predetermined distance of the user:
      determining a corrective sensory stimulation that is configured to offset balance of the user in a direction away from the obstacle; and
      outputting the corrective sensory stimulation to a sensory user device; and
   in response to determining that the obstacle is present in the survey area of the surface outside of the predetermined distance of the user, performing another survey of the surface after a predetermined amount of time has elapsed,
   wherein the another survey considers at least the previous determination that the obstacle is present in the survey area of the surface outside of the predetermined distance of the user.

2. The computer-implemented method as recited in claim 1, wherein the corrective sensory stimulation is output when the user is positioned about one average stride of the user from contacting the obstacle.

3. The computer-implemented method as recited in claim 1, wherein the corrective sensory stimulation is galvanic vestibular stimulation.

4. The computer-implemented method as recited in claim 1, wherein the corrective sensory stimulation is output with an audio and/or visual warning of the obstacle to the sensory user device.

5. The computer-implemented method as recited in claim 1, wherein an amount of corrective sensory stimulation output is determined based on at least one user trait selected from the group consisting of: an average stride distance of the user, a body weight of the user, a height of the user, a walking speed of the user, and an age of the user.

6. The computer-implemented method as recited in claim 1, wherein determining whether the obstacle is present includes performing recognition of an obstacle selected from the group consisting of: a hole, an object above the surface within the survey area, a cord, a stair, a slope, and liquid.

7. The computer-implemented method as recited in claim 1, wherein the survey is performed using a surface monitoring wearable camera.

8. The computer-implemented method as recited in claim 1, wherein the sensory user device includes a galvanic vestibular stimulation enabled headphone.

9. A computer program product that is configured to prevent user falls, the computer program product comprising a computer readable storage medium having program instructions embodied therewith, wherein the computer readable storage medium is not a transitory signal per se, the program instructions are readable and/or executable by a computer to cause the computer to perform a method comprising: performing, by the computer, a survey of a survey area of a surface in an intended direction of travel of a user;
   determining, by the computer, whether an obstacle is present in the survey area of the surface within a predetermined distance of the user;
   in response to determining, by the computer, that an obstacle is present in the survey area of the surface within the predetermined distance of the user, performing, by the computer, the following process until it is determined that the obstacle is not present in the survey area of the surface within the predetermined distance of the user:
      determining a corrective sensory stimulation that is configured to offset balance of the user in a direction away from the obstacle; and
      outputting the corrective sensory stimulation to a sensory user device; and
   in response to determining, by the computer, that the obstacle is present in the survey area of the surface outside of the predetermined distance of the user, performing, by the computer, another survey of the surface after a predetermined amount of time has elapsed,
   wherein the another survey considers at least the previous determination that the obstacle is present in the survey area of the surface outside of the predetermined distance of the user.

10. The computer program product as recited in claim 9, wherein the corrective sensory stimulation is output when the user is positioned about one average stride of the user from contacting the obstacle.

11. The computer program product as recited in claim 9, wherein the corrective sensory stimulation is galvanic vestibular stimulation.

12. The computer program product as recited in claim 9, wherein the corrective sensory stimulation is output with an audio and/or visual warning of the obstacle to the sensory user device.

13. The computer program product as recited in claim 9, wherein an amount of corrective sensory stimulation output is determined based on at least one user trait selected from the group consisting of: an average stride distance of the user, a body weight of the user, a height of the user, a walking speed of the user, and an age of the user.

14. The computer program product as recited in claim 9, wherein the survey is performed using a surface monitoring wearable camera.

15. The computer program product as recited in claim 9, wherein the sensory user device includes a galvanic vestibular stimulation enabled headphone.

16. An apparatus, comprising:
   a camera that is configured to capture image data of a survey area of a surface in a direction of travel of a user;
   a processor coupled to the camera, wherein the processor is configured to:
      analyze the image data to determine whether an obstacle is present in the survey area of the surface within a predetermined distance of the user;
      in response to determining an obstacle is present in the survey area of the surface within the predetermined distance of the user, output an instruction to apply a corrective sensory stimulation that is configured to offset balance of the user in a direction away from the obstacle; and
      in response to determining that the obstacle is present in the survey area of the surface outside of the predetermined distance of the user, analyzing additional image data of the survey area, the additional image data being captured by the camera after a predetermined amount of time has elapsed since the determination that the obstacle is present in the survey area of the surface outside of the predetermined distance of the user, wherein analyzing the additional image data considers at least the previous determination that the obstacle is present in the survey area of the surface outside of the predetermined distance of the user; and
   a sensory user device coupled to the processor, wherein the sensory user device is configured to apply the corrective sensory stimulation to the user in response to receiving the instruction.

* * * * *